US00PP26736P2

(12) United States Plant Patent
Kamstra

(10) Patent No.: US PP26,736 P2
(45) Date of Patent: May 17, 2016

(54) *STACHYS* PLANT NAMED "BAREIGHTYFOUR"

(50) Latin Name: ***Stachys byzantina*×*Stachys debilis***
Varietal Denomination: Bareightyfour

(71) Applicant: Silvan Kamstra, Aalsmeer (NL)

(72) Inventor: Silvan Kamstra, Aalsmeer (NL)

(73) Assignee: Bartels Stek B.V., Aalsmeer (NL)

( * ) Notice: Subject to any disclaimer, the term of this patent is extended or adjusted under 35 U.S.C. 154(b) by 117 days.

(21) Appl. No.: 14/120,665

(22) Filed: Jun. 14, 2014

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — C. A. Whealy

(57) ABSTRACT

A new and distinct cultivar of *Stachys* plant named 'Bareightyfour', characterized by its compact and upright plant habit; vigorous growth habit; and densely pubescent recurved leaves.

1 Drawing Sheet

Botanical designation: *Stachys byzantina*×*Stachys debilis*.
Cultivar denomination: 'BAREIGHTYFOUR'.

BACKGROUND OF THE INVENTION

The present invention relates to a new and distinct cultivar of *Stachys* plant, botanically known as *Stachys byzantina*× *Stachys debilis* and hereinafter referred to by the name 'Bareightyfour'.

The new *Stachys* plant is a product of a planned breeding program conducted by the Inventor in Aalsmeer, The Netherlands. The objective of the breeding program was to create new compact *Stachys* plants with unique and attractive leaves.

The new *Stachys* plant originated from a cross-pollination made by the Inventor in 2009 in Aalsmeer, The Netherlands, of a proprietary selection of *Stachys byzantina*×*Stachys debilis* identified as code number ST014, not patented, as the female, or seed, parent with a proprietary selection of *Stachys byzantina*×*Stachys debilis* identified as code number ST002, not patented, as the male, or pollen, parent. The new *Stachys* plant was discovered and selected by the Inventor as a single plant from within the progeny of the stated cross-pollination in a controlled environment in Aalsmeer, The Netherlands in 2010.

Asexual reproduction of the new *Stachys* plant by cuttings in a controlled environment in Aalsmeer, The Netherlands since 2010 has shown that the unique features of this new *Stachys* plant are stable and reproduced true to type in successive generations.

SUMMARY OF THE INVENTION

Plants of the new *Stachys* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Bareightyfour'. These characteristics in combination distinguish 'Bareightyfour' as a new and distinct *Stachys* plant:

1. Compact and upright plant habit.
2. Vigorous growth habit.
3. Densely pubescent recurved leaves.

Plants of the new *Stachys* and the parent selections differ primarily in plant and growth habit.

Plants of the new *Stachys* can be compared to plants of *Stachys aethiopica* 'NM 001', disclosed in U.S. Plant Pat. No. 17,859. Plants of the new *Stachys* and 'NPN 001' differ primarily in plant and growth habit. In addition, plants of the new *Stachys* do not produce flowers whereas plants of 'NPN 001' are freely-flowering.

BRIEF DESCRIPTION OF THE PHOTOGRAPH

The accompanying colored photograph illustrates the overall appearance of the new *Stachys* plant showing the colors as true as it is reasonably possible to obtain in colored reproductions of this type. Colors in the photograph may differ slightly from the color values cited in the detailed botanical description which accurately describe the colors of the new *Stachys* plant.

The photograph comprises a side perspective view of typical flowering stem of 'Bareightyfour' grown in a container.

DETAILED BOTANICAL DESCRIPTION

The aforementioned photograph and following observations, measurements and values describe plants grown during the winter in 17-cm containers in a glass-covered greenhouse in Aalsmeer, The Netherlands and under cultural practices typical of commercial *Stachys* production. During the production of the plants, day temperatures averaged 15° C. and night temperatures averaged 10° C. Plants were six months old when the photograph and description were taken. In the following description, color references are made to The Royal Horticultural Society Colour Chart, 2001 Edition, except where general terms of ordinary dictionary significance are used.

Botanical classification: *Stachys byzantina*×*Stachys debilis* 'Bareightyfour'.

Parentage:

*Female, or seed, parent*.—Proprietary selection of *Stachys byzantina*×*Stachys debilis* identified as code number ST014, not patented.

*Male, or pollen, parent*.—Proprietary selection of *Stachys byzantina*×*Stachys debilis* identified as code number ST002, not patented.

Propagation:

*Type*.—By cuttings.

*Root description*.—Fine, fibrous; white in color.

*Rooting habit*.—Freely branching; medium density.

Plant description:

*Plant and growth habit*.—Herbaceous perennial typically grown as a foliage plant; compact and upright plant habit; vigorous growth habit.

*Plant height*.—About 25 cm.

*Plant width* (*spread*).—About 25 cm.

*Lateral branches*.—Length: About 30 cm. Internode length: About 1 mm. Strength: Strong. Aspect: Upright to outwardly. Texture: Pubescent. Color: Greenish grey.

Leaf description:

*Arrangement*.—Alternate, simple.

*Length*.—About 25 cm.

*Width*.—About 4 cm.

*Shape*.—Lanceolate, recurved.

*Apex*.—Acute.

*Base*.—Acuminate.

*Margin*.—Entire.

*Texture, upper and lower surfaces*.—Densely pubescent.

*Venation pattern*.—Parallel.

*Color*.—Developing leaves, upper and lower surfaces: Close to 155C. Fully expanded leaves, upper surface: Close to 139B and 156A; venation, close to 139B. Fully expanded leaves, lower surface: Close to 139B and 156A; venation, close to 139B and 156A.

*Petioles*.—Length: About 10 cm. Diameter: About 5 mm. Texture, upper and lower surfaces: Pubescent. Color, upper and lower surfaces: Close to 156A and 139B.

Flower description: To date, flower initiation and development has not been observed on plants of the new *Stachys*.

Pathogen & pest resistance: Plants of the new *Stachys* have not been observed to be resistant to pathogens and pests common to *Stachys* plants.

It is claimed:

1. A new and distinct *Stachys* plant named 'Bareightyfour' as illustrated and described.

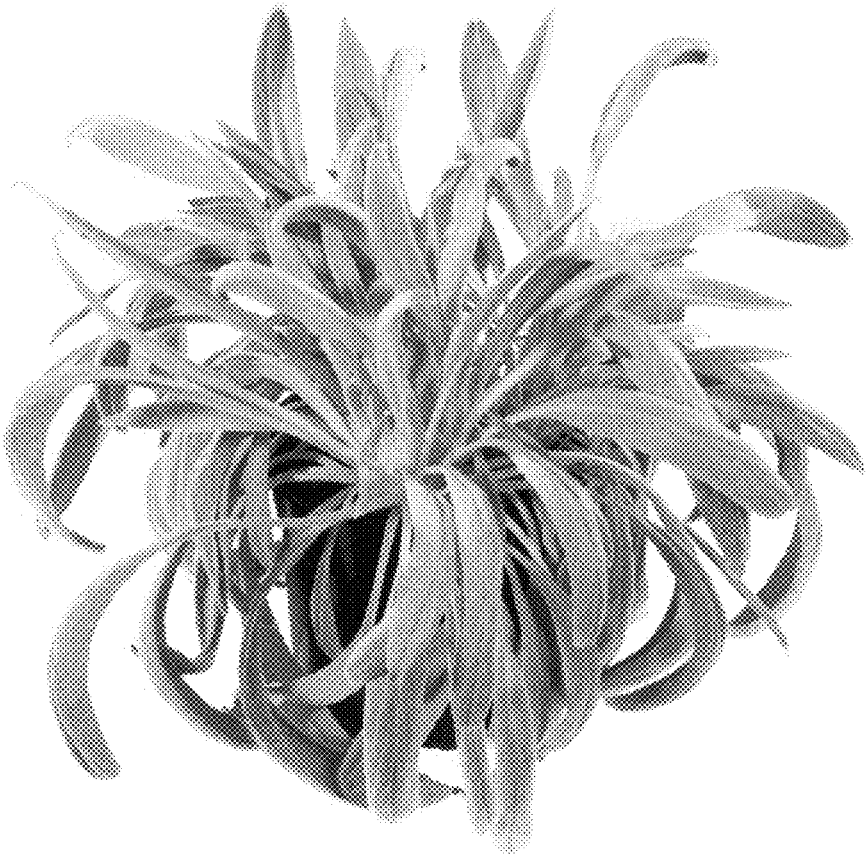

* * * * *